(12) United States Patent
Stingl et al.

(10) Patent No.: US 7,723,047 B2
(45) Date of Patent: May 25, 2010

(54) METHOD FOR THE DISCRIMINATION AND ISOLATION OF MAMMARY EPITHELIAL STEM AND COLONY-FORMING CELLS

(75) Inventors: John Stingl, Vancouver (CA); Connie J. Eaves, Vancouver (CA)

(73) Assignees: Stemcell Technologies Inc., Vancouver, British Columbia (CA); British Columbia Cancer Agency Branch, Vancouver, British Columbia (CA)

( * ) Notice: Subject to any disclaimer, the term of this patent is extended or adjusted under 35 U.S.C. 154(b) by 120 days.

(21) Appl. No.: 11/758,964

(22) Filed: Jun. 6, 2007

(65) Prior Publication Data
US 2008/0032402 A1 Feb. 7, 2008

Related U.S. Application Data

(63) Continuation-in-part of application No. 11/447,956, filed on Jun. 7, 2006.

(60) Provisional application No. 60/689,105, filed on Jun. 10, 2005.

(51) Int. Cl.
G01N 33/53 (2006.01)
C12N 5/08 (2006.01)
(52) U.S. Cl. ........................................ 435/7.1; 435/372
(58) Field of Classification Search ................... None
See application file for complete search history.

(56) References Cited

U.S. PATENT DOCUMENTS 6,306,575 B1 * 10/2001 Thomas et al. .................. 435/2
6,491,917 B1 * 12/2002 Thomas et al. ............ 424/140.1

FOREIGN PATENT DOCUMENTS

WO WO 2005/021728 * 10/2005

OTHER PUBLICATIONS

Al-Hajj M, Wicha MS, Benito-Hernandez A, Morrison SJ and Clarke MF. Prospective identification of tumorigenic breast cancer cells. Proc Natl Acad Sci U S A. 2003, 100(7):3983-8.
Asselin-Labat M-L, Shackleton M, Stingl J, Vaillant F, Forrest NC, Eaves CJ, Visvader JE and Lindeman G. Steroid hormone receptor status of mouse mammary stem cells. JNCI 2006, 98(14):1011-4.
Barclay AN, Brown MH, Law SKA, McKnight AJ, Tomlinson MG, Van Der Merwe PA (Eds.) CD24. In: The Leukocyte Antigen Facts Book. Academic Press Inc., San Diego, USA, pp. 192-193, 1997.
Barclay AN, Brown MH, Law SKA, McKnight AJ, Tomlinson MG, Van Der Merwe PA (Eds.) CD31. In: The Leukocyte Antigen Facts Book. Academic Press Inc., San Diego, USA, pp. 206-208, 1997.
Barclay AN, Brown MH, Law SKA, McKnight AJ, Tomlinson MG, Van Der Merwe PA (Eds.) CD45. In: The Leukocyte Antigen Facts Book. Academic Press Inc., San Diego, USA, pp. 244-247, 1997.
Barclay AN, Brown MH, Law SKA, McKnight AJ, Tomlinson MG, Van Der Merwe PA (Eds.) CD49f. In: The Leukocyte Antigen Facts Book. Academic Press Inc., San Diego, USA, pp. 267-268, 1997.
Baumann P, Cremers N, Kroese F, Orend G, Chiquet0ehrismann R, Uede T, Yagita H and Sleeman JP. CD24 expression causes the acquisition of multiple cellular propertiess associated with tumor growth and metastasis. Cancer Research 2005, 65(23):10783-93.
Carter WG, Kaur P, Gil SG, Gahr PJ and Wayner EA. Distinct functions for integrins alpha 3 beta 1 in focal adhesions and alpha 6 beta 4/bullous pemphigoid antigen in a new stable anchoring contact (SAC) of keratinocytes: relation to hemidesmosomes. J Cell Biol. 1990: 111(6 Pt 2), 3141-54.
Clarke C, Titley J, Davies S and O'Hare MJ. An immunomagnetic separation method using superparamagnetic (MACS) beads for large-scale purification of human mammary luminal and myoepithelial cells. Epithelial Cell Biol 1994, 3(1):38-46.
Crowley MR, Bowtell D and Serra R. TGF-β, c-Cbl, and PDGFR-α in the mammary stroma. Developmental Biology 2005, 279:58-72.
Deugnier M-A, Faraldo MM, Teuliere J, Thiery JP, Medina D and Glukhova MA. Isolation of mouse mammary epithelial progenitor cells with basal characteristics from the Comma-DB cell line. Developmental Biology 2006, 293(2):414-25.
Dundas SR, Ormerod MG, Gusterson BA, O'Hare MJ. Characterization of luminal and basal cells flow-sorted from the adult rat mammary parenchyma. J Cell Sci 1991, 100(Pt 3):459-71.
Fridriksdottir AJR, Villadsen R, Gudjonsson T and Petersen OW. Maintenance of cell type diversification in the human breast. Journal of Mammary Gland Biology and Neoplasia 2005, 10(1):61-74.
Hebbard L, Steffen A, Zawadzki V, Fieber C, Howells N, Moll J, Ponta H, Hofmann M and Sleeman J. CD44 expression and regulation during mammary gland development and function. Journal of Cell Science 2000, 113(Pt 14):2619-30.
Kao CY, Nomata K, Oakley CS, Welsch CW and Chang CC. Two types of normal human breast epithelial cells derived from reduction mammoplasty: phenotypic characterization and respose to SV40 transfection. Carcinogenesis 1995, 16(3):531-38.

(Continued)

*Primary Examiner*—Michail A Belyavskyi
(74) *Attorney, Agent, or Firm*—Bereskin & Parr LLP/S.E.N.C.R.L., s.r.l.; Micheline Gravelle (57) ABSTRACT

The present invention relates to an improved method that permits the differential isolation of mouse mammary stem cells and colony forming cells (CFCs). The method involves depletion of non-epithelial cells from freshly dissociated mouse mammary tissue by incubation with an antibody composition containing antibodies specific for CD45, Ter119, CD35 and optionally CD140a. After formation of conjugates between the non-epithelial mammary cells and the antibodies specific for CD45, Ter119, CD35 and optionally CD140a, the cell conjugates are removed and the remaining epithelial cells are then incubated with an antibody composition containing antibodies specific for CD24 and CD49f or CD24 and CD14. After formation of conjugates between the epithelial cells and the antibodies specific for CD24 and CD49f or CD24 and CD14, the mouse mammary stem and the luminal-restricted CFC cells can be differentially isolated. The invention also relates to kits for carrying out this method and to the cell preparations prepared by this method.

15 Claims, 6 Drawing Sheets

OTHER PUBLICATIONS

Kao CY, Oakley CS, Welsch CW, Chang CC. Growth requirements and neoplastic transformation of two types of normal human breast epithelial cells derived from reduction mammoplasty. In Vitro Cell Dev Biol Anim 1997, 33(4):282-88.

Kemshead JT. Immunomagnetic manipulation of hematopoietic cells: A review of current technology. Journal of Hematotherapy 1992, 1(1):35-44.

Kim ND and Clifton KH. Characterization of rat mammary epithelial cell subpopulations by peanut lectin and anti-Thy-1.1 antibody and study of flow-sorted cells in vivo. Experimental Cell Res 1993, 207(1):74-85.

Kina T, Ikuta K, Takayama E, Wada K, Majumdar AS, Weissman IL and Katsura Y. The monoclonal antibody TER-119 recognizes a molecule associated with glycophorin A and specifically marks the late stages of murine erythroid lineage. Br J Haematol. 2000, 109(2):280-7.

Kordon EC and Smith GH. An entire functional mammary gland may comprise the progeny from a single cell.Development 1998, 125(10):1921-30.

Li Y and Rosen JM. Stem/progenitor cells in mouse mammary gland development and breast cancer. Journal of Mammary Gland Biology and Neoplasia 2005, 10(1):17-24.

Lipscomb EA, Simpson KJ, Lyle SR, Ring JE, Dugan AS and Mercurio AM. The $\alpha6\beta4$ integrin maintains the survival of human breast carcinoma cells in vivo. Cancer Research 2005, 65(23):10970-6.

Liu S, Dontu G, Mantle ID, Patel S, Ahn N-S, Jackson KW, Suri P and Wicha MS, Hedgehog signaling and Bmi-1 regulate self-renewal of normal and malignant human mammary stem cells. Cancer Research 2006, 66(12):6063-71.

O'Hare MJ, Ormerod MG, Monaghan P, Lane EB, and Gusterson BA. Characterization in vitro of luminal and myoepithelial cells isolated from the human mammary gland by cell sorting.Differentiation 1991, 46(3):209-21.

Orr-Urtreger A and Lonai P. Platelet-derived growth factor-A and its receptor are expressed in separate, but adjacent cell layers of the mouse embryo. Development. 1992, 115(4):1045-58.

Paguirigan A, Beebe DJ, Liu B and Alexander C. Mammary stem and progenitor cells: tumour precursors? Eur J Cancer 2006, 42(9):1225-36.

Ponti D, Costa A, Zaffaroni N, Pratesi G, Petrangolini G, Coradini D, Pilotti S, Pierotti MA and Daidone MG. Isolation and in vitro propagation of tumorigenic breast cancer cells with stem/progenitor cell properties. Cancer Research 2006, 65(13):5506-11.

Shackleton M, Vaillant F, Simpson KJ, Stingl J, Smyth GK, Asselin-Labat ML, Wu L, Lindeman GJ and Visvader JE. Generation of functional mammary gland from a single stem cell. Nature 2006, 439(7072):84-8.

Shackleton M, Vaillant F, Simpson KJ, Stingl J, Smyth GK, Asselin-Labat M-L, Wu L, Visvader JE and Lindeman GJ. Generation of a functional mammary gland from a single stem cell. Proceedings of the AACR. vol. 47, Apr. 2006, p. 1136, (abstract).

Shulewitz M, Soloviev I, Wu T, Koeppen H, Polakis P. and Sakanaka C. Repressor roles for TCF-4 and Sfrp1 in Wnt signaling in breast cancer. Oncogene 2006, 25(31):4361-9.

Sleeman KE, Kendrick H, Ashworth A, Isacke CM and Smalley MJ. CD24 staining of mouse mammary gland cells defines luminal epithelial, myoepithelial/basal and non-epithelial cells. Breast Cancer Research 2006, 8(1):R7.

Smalley MJ and Clarke RB. The mammary gland "side population": A putative stem/progenitor cell marker? Journal of Mammary Gland Biology and Neoplasia 2005, 10(1):37-47.

Smalley MJ, Titley J and O'Hare MJ. Clonal characterization of mouse mammary luminal epithelial and myoepithelial cells separated by fluorescence-activated cell sorting. In Vitro Cell Dev Biol-Animal 1998, 34(9):711-721.

Smith GH and Boulanger CA. Mammary epithelial stem cells: transplantation and self-renewal analysis. Cell Prolif. 2003, 36(Suppl. 1):3-15.

Stingl J, Eaves CJ, Emerman JT, Choi D, Woodside WM and Peters CE. Column-free FACS-compatible immunomagnetic enrichment of Ep-CAM positive and CD49f positive human mammary epithelial progenitor cells. Proceedings of the AACR, vol. 44, Mar. 2003, p. 987. (abstract).

Stingl J, Eaves CJ, Emerman JT. IN: Ip M and Asch BB, Ed. Methods in Mammary Gland Biology and Breast Cancer Research. New York (NY):Kluwer Academic/Plenum Publishers, 2000:177-93.

Stingl J, Eaves CJ, Kuusk U, Emerman JT. Phenotypic and functional characterization in vitro of a multipotent epithelial cell present in the normal adult human breast.Differentiation. 1998, 63(4):201-13.

Stingl J, Eirew P, Ricketson I, Shackleton M, Vaillant F, Choi D, Li HI and Eaves CJ. Purification and unique properties of mammary epithelial stem cells. Nature 2006, 439(7079):993-7.

Stingl J, Emerman JT, Cunha G and Eaves CJ. Phenotypic characterization of a rare subpopulation of human mammary epithelial cells using a novel in vivo xenotransplantation assay. Proceedings of the AACR, vol. 44, Mar. 2003, p. 987. (abstract).

Stingl J, Raouf A, Emerman JT and Eaves CJ. Epithelial progenitors in the normal human mammary gland. Journal of Mammary Gland Biology and Neoplasia 2005, 10(1):49-59.

Stingl J, Ricketson I, Choi D and Eaves CJ. Phenotypic characterization of mouse mammary stem and progenitor cells. Final Program and Abstract Book, Stem Cell Network AGM 2004, Montreal, QC, Nov. 3-5, 2004, p. 39. (abstract).

Stingl J, Ricketson I, Choi D and Eaves CJ. Quantitation and phenotypic characterization of mouse mammary stem cells. Proceedings of the AACR, vol. 44, Mar. 2003, p. 988. (abstract).

Stingl J, Ricketson I, Choi D and Eaves CJ. Phenotypic characterization of mouse mammary stem and progenitor cells. 2nd Annual Meeting ISSCR 2004, Boston, MA, Jun. 10-13, 2004, p. 31. (abstract).

Stingl J, Ricketson I, Choi D and Eaves CJ. Phenotypic characterization of mouse mammary stem and progenitor cells. Proc Am Assoc Cancer Res 2004, 45:641-2. (abstract).

Stingl J, Ricketson I, Choi D and Eaves CJ. Purification of the adult pluripotent self-renewing mouse mammary stem cell using an in vivo assay. Proceedings of the AACR, vol. 46, Mar. 2005, p. 1240 (abstract).

Stingl J, Zandieh I, Eaves CJ, Emerman JT. Characterization of bipotent mammary epithelial progenitor cells in normal adult human breast tissue.Breast Cancer Res Treat 2001, 67(2):93-109.

Welm B, Behbod F, Goodell MA and Rosen JM. Isolation and characterization of functional mammary gland stem cells. Cell Prolif. 2003, 36(S1):17-32.

Welm BE, Tepera SM, Venezia T, Graubert TA, Rosen JM and Goodell MA. Sca-1(pos) cells in the mouse mammary gland represent an enriched progenitor cell population. Dev Biol 2002; 245(1):42-56.

Wicha MS, Dontu G, Al-Hajj M and Clarke MF. Stem cells in the normal and cancerous human breast. Plenary Lecture presented at the 26th Annual San Antonio Breast Cancer Symposium. Dec. 3, 2003. Abstract published in Breast Cancer Research and Treatment. vol. 82 (S1), 2003.

Woodward WA, Chen MS, Behbod F and Rosen JM. On mammary stem cells. Journal of Cell Science 2005, 118 (Pt 16):3585-94.

\* cited by examiner

METHOD FOR THE DISCRIMINATION AND ISOLATION OF MAMMARY EPITHELIAL STEM AND COLONY-FORMING CELLS

This application is a continuation in part of U.S. patent application Ser. No. 11/447,956, filed on Jun. 7, 2006, which claims the benefit under 35 USC §119(e) from U.S. provisional patent application Ser. No. 60/689,105, filed Jun. 10, 2005. Both applications are incorporated herein by reference.

FIELD OF THE INVENTION

The present invention relates to novel antibody compositions, and processes and kits for preparing cell preparations of different subsets of mouse mammary cells, and the use of the cell preparations in the study of cell biology and cancer.

BACKGROUND OF THE INVENTION

The mammary gland is a compound tubulo-alveolar gland that is composed of a series of branched ducts that, during lactation, drain sac-like alveoli (lobules). In the rodent, the mammary epithelium is embedded within a mammary fat pad rich in stromal (non-epithelial cells). The mammary epithelium is composed of two lineages of epithelial cells: the luminal cells (which make milk during lactation) and basal positioned myoepithelial cells. Generation and maintenance of the mammary epithelium is via the mammary stem cell (MaSC), which is defined here as that cell that can generate both the ductal and lobular structures of the mammary gland, can generate all the cell lineages of the mammary epithelium and can self-renew. The MaSC is of interest to the breast cancer biologist since cancer theory suggests that it is the stem cell, and possibly some of its more immediate descendants that have decreased stem cell potential but still have proliferative potential that are the targets for malignant transformation. As well, recent publications in the literature demonstrate that malignancies themselves have a stem cell component that propagates the tumor (Al-Hajj M, Wicha M S, Benito-Hernandez A, Morrison S J, Clarke M F. Proc Natl Acad Sci USA. 2003; 100:3983-8). This has huge implications in the treatment of cancer since it suggests that in order for cancer to be successfully contained or eradicated, it is the tumor stem cell component that has to be the therapeutic target. The ability to identify and purify mammary stem cells as well as mammary cells with high proliferative capacity but not necessarily having stem cell properties would be invaluable to the study of breast cancer and epithelial cell tumor biology.

In 1998 an experiment was performed which definitively demonstrated that a cell exists within the mouse mammary gland that fulfils the criteria of a MaSC (Kordon E C, Smith G H. Development 1998; 125:1921-30). Our own experiments involving transplantation of freshly isolated non-cultured mammary epithelial cells obtained from adult female mice into recipient mice indicates that MaSC occur at a frequency of about 1 cell in 1,300 total mammary cells and that there are approximately 1,400 MaSC per gland in the mouse.

There have been a number of in vitro studies trying to characterize the cells with proliferative potential in the human, mouse and rat mammary glands in a hope to identify the mammary stem cell. These experiments typically involve seeding phenotypically distinct subtypes of mammary cells at clonal densities in culture dishes in order to identify cells with growth potential by their ability to form colonies. Cells with the potential to form colonies in vitro are termed colony-forming cells (CFCs), and these assays detect all cells that have growth potential, regardless if they are stem cells or not. The inventors research data has demonstrated that the majority (>90%) of CFCs are not stem cells, but cells with growth potential that reside lower in the cellular hierarchy than stem cells. CFCs themselves can be subdivided into different subtypes such as luminal-restricted CFCs (which can only give rise to luminal cells) and bipotent CFCs (which can generate both luminal and myoepithelial cells). In the mouse mammary gland, approximately 90% of all CFCs are of the luminal-restricted type. The phenotypes of mammary CFCs isolated from different species are summarized in Table I.

These in vitro studies to characterize CFCs are limited because colony assays, in their current state, are unable to identify MaSC and to discriminate between MaSC that generate colonies from other CFCs that are deficient in stem cell properties.

The first insight into the phenotype of MaSC was reported by Welm and colleagues who demonstrated that expression of the cell surface molecule Sca-1 enriches for MaSCs that generate ductal-lobular outgrowths when transplanted into the cleared mammary fat pads of recipient mice (Welm B E, Tepera S B, Venezia T, Graubert T A, Rosen J M, Goodell M A. Dev Biol 2002; 245:42-56). However this is a crude enrichment strategy since approximately 20-60% of all mammary cells express Sca-1, and thus MaSC are far from being purified in Sca-1$^+$ enriched subpopulations. To date, there has been no description of a method in the prior art that permits the isolation to high purity of stromal, luminal, myoepithelial, CFCs and MaSC subpopulations of mammary cells. The current method of invention satisfies this need.

SUMMARY OF THE INVENTION

The present invention relates to antibody compositions and methods that can be used to separate non-epithelial cells from epithelial cells in a sample containing mammary cells. The present inventors have developed antibody compositions and a method that can be used to identify the following mammary cell subtypes:
  Stromal (non-epithelial); and
  Epithelial, which comprise the subtypes:
    Luminal;
    Myoepithelial;
    Luminal-restricted CFC; and
    MaSC.

The present invention relies on the observation that mammary stem cells (MaSC) express CD24 and high levels of CD49f (α-6 integrin), but do not express the hematopoietic markers CD45, Ter119 and the endothelial marker CD31. Enrichment of mammary cells on the basis of this strategy (CD45$^-$/Ter119$^-$/CD31$^-$/CD49f$^{++}$/CD24$^+$) as outlined this patent application results in a purity of about 1 MaSC in 20 sorted cells. CD140a is a marker expressed by many of the mammary stromal cells and some mammary cells (Crowley M. R., Bowtell D and Serra R. Dev Biol 2005; 279: 58-72). Inclusion of CD140a into the stromal cell-depletion cocktail results in similar MaSC purities following FACS. Although the use of the markers CD45, Ter119, CD31 and CD140a is not essential to isolate MaSCs and CFCs, their use is beneficial since many of these cells types co-express CD24 and CD49f and thus can decrease the purity of stem and CFC cell enriched fractions. This is particularly so in mammary cell preparations with high levels of stromal cell contamination.

Accordingly, the present invention provides a method of separating non-epithelial cells from epithelial cells in a sample containing mammary cells comprising 1) reacting the sample with an antibody composition capable of binding to antigens on non-epithelial cells under conditions so that conjugates are formed between the antibodies and the cells in the sample containing the non-epithelial antigens; 2) removing the conjugates; and 3) recovering a cell preparation which is enriched in mammary epithelial cells.

The antibody composition used to isolate non-epithelial cells preferably comprises antibodies that bind to CD45, Ter119, CD31 and optionally CD140a.

In a preferred embodiment, the method is used to enrich for mammary stem cells or luminal restricted colony forming cells. Accordingly, the present inventions provides a method of enriching for mammary stem cells or luminal restricted colony forming cells in a sample containing mammary cells comprising 1) reacting the sample with a first antibody composition capable of binding to antigens on non-epithelial cells under conditions so that conjugates are formed between the antibodies and the cells in the sample containing the non-epithelial antigens; 2) removing the conjugates; 3) recovering a cell preparation which is enriched in mammary epithelial cells; and 4) reacting the sample enriched in epithelial cells with a second antibody composition capable of binding the antigens CD24 and/or CD49f under conditions so that conjugates form between antibodies and the cells in the sample containing the antigens CD24 and/or CD49f; and 5) recovering cells that are bound by the antibodies.

The inventors have also determined that CD14 is strongly expressed among some of the luminal mammary epithelial cells and that approximately 89% of all Ma-CFCs in the luminal compartment express CD14. The inventors have also demonstrated that the CD14 gene transcript is upregulated in the Ma-CFC population. In addition, the inventors have found that the CD14+ luminal progenitor population can be further subdivided into cells that are $Sca1^{high}$ and $Sca1^{low}$. Both the $CD14^+Sca1^{high}$ and $CD14^+Sca1^{low}$ subpopulations contain progenitor cells.

Accordingly, in a specific embodiment, the method is used to enrich for mammary luminal restricted colony forming cells. Accordingly, the present invention provides a method of enriching for luminal restricted colony forming cells in a sample containing mammary cells comprising 1) reacting the sample with a first antibody composition capable of binding to antigens on non-epithelial cells under conditions so that conjugates are formed between the antibodies and the cells in the sample containing the non-epithelial antigens; 2) removing the conjugates; 3) recovering a cell preparation which is enriched in mammary epithelial cells; 4) reacting the sample enriched in epithelial cells with a second antibody composition capable of binding the antigens CD24 and/or CD14 under conditions so that conjugates form between antibodies and the cells in the sample containing the antigens CD24 and/or CD14; and 5) recovering the conjugates wherein the cells in the conjugates comprise luminal restricted colony forming cells.

The present invention also relates to a kit useful in performing the process of the invention and instructions for performing the process of the invention. The invention further relates to cell preparations obtained in accordance with the process of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

I. Definitions

The term "differentiated cells" used herein refers to mouse mammary cells which have limited or no proliferative capacity. The differentiated cells represent the specialized end cells that serve a specific function. In the case of the mammary gland, these cells are the luminal cells and the myoepithelial cells.

Figure 1:
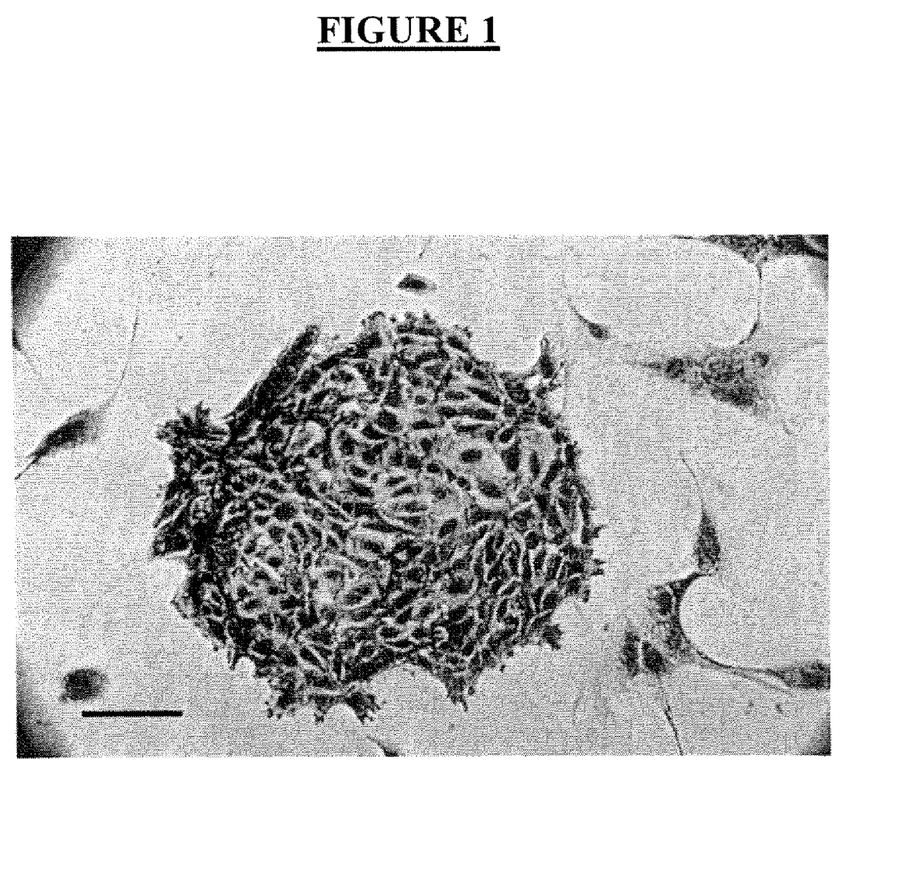
FIG. 1: Six day-old pure luminal cell colony grown in vitro.

The term "colony-forming cells" or "CFCs", also known as "progenitor cells" used herein refers to cells which are the immediate precursors to the differentiated cells. They have extensive proliferative capacity. In the mouse mammary gland, approximately 90% of all CFCs have a luminal cell phenotype and give rise to only pure luminal epithelial cell colonies. Mammary CFCs can be detected by their ability to generate colonies in vitro. FIG. 1 illustrates a pure luminal cell colony generated after 6 days of culture.

The term "stem cells" used herein refers the cells that give rise to the CFCs. Mammary stem cells (MaSC) are defined as those cells that can generate both the ductal and lobular structures of the mammary gland, can generate all the cell lineages of the mammary epithelium and can self-renew.

The term "antibody" is understood to include monoclonal antibodies and polyclonal antibodies, antibody fragments (e.g., Fab, and $F(ab')_2$) and recombinantly produced binding partners. Antibodies are understood to be reactive against a selected antigen on the surface of a cell if they bind with an affinity (association constant) of greater than or equal to $10^7$ $M^{-1}$.

II. Methods and Compositions

The present invention provides a method of separating non-epithelial cells from epithelial cells in a sample containing mammary cells comprising 1) reacting the sample with an antibody composition capable of binding to antigens on non-epithelial cells under conditions so that conjugates are formed between the antibodies and the cells in the sample containing the non-epithelial antigens; 2) removing the conjugates; and 3) recovering a cell preparation which is enriched in mammary epithelial cells.

In a preferred embodiment, the method is used to enrich for mammary stem cells or luminal restricted colony forming cells. Accordingly, the present inventions provides a method of enriching for mammary stem cells or luminal restricted colony forming cells in a sample containing mammary cells comprising 1) reacting the sample with a first antibody composition capable of binding to antigens on non-epithelial cells under conditions so that conjugates are formed between the antibodies and the cells in the sample containing the non-epithelial antigens; 2) removing the conjugates; 3) recovering a cell preparation which is enriched in mammary epithelial cells; and 4) reacting the sample enriched in epithelial cells with a second antibody composition capable of binding the antigens CD24 and/or CD49f under conditions so that conjugates form between antibodies and the cells in the sample containing the antigens CD24 and/or CD49f; and recovering cells that are bound by the antibodies.

The antibody composition used to isolate non-epithelial cells preferably comprises antibodies that bind to CD45, Ter119, CD31 and optionally CD140a.

CD45 and Ter119 are cell surface proteins that are preferentially expressed by cells of the hematopoietic system (CD45. In: The Leukocyte Antigen Facts Book. Barclay A N, Brown M H, Law S K A, McKnight A J, Tomlinson M G van der Merwe P A (Eds.) Academic Press Inc., San Diego, USA, pp 244-47, 1997; Kina T, Ikuta K, Takayama E, Wada K, Majumdar A S, Weissman I L, Katsura Y. Br J Haematol. 2000; 109: 280-7). CD31 is a cell surface protein that is preferentially, but not exclusively expressed by endothelial cells (CD31. In: The Leukocyte Antigen Facts Book. Barclay A N, Brown M H, Law S K A, McKnight A J, Tomlinson M G van der Merwe P A (Eds.) Academic Press Inc., San Diego, USA, pp 206-8, 1997), whereas CD140a is a cell surface protein that is preferentially, but not exclusively expressed by stromal cells (Orr-Urtreger A, Lonai P. Development. 1992; 115:1045-58). It is expressed by some cells of the mammary epithelium (Crowley M. R., Bowtell D. and Serra R. Dev Biol 2005; 279:58-72).

Figure 2:
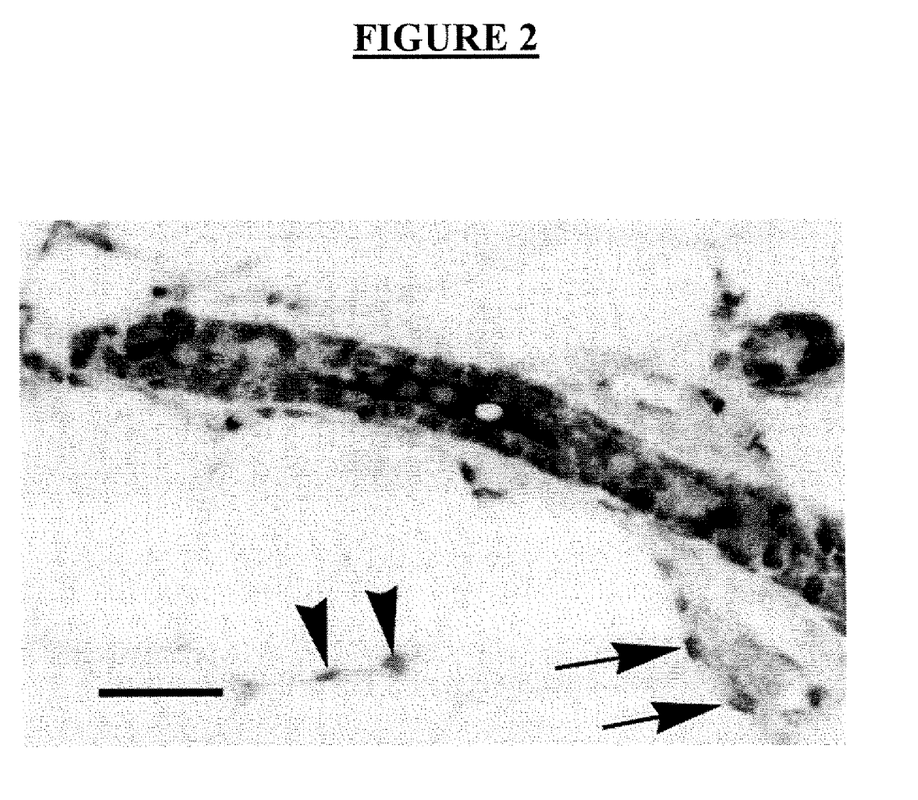
FIG. 2: Expression of CD24 among cells of the mouse mammary gland. Arrows indicate $CD24^+$ endothelial cells and arrowheads indicate $CD24^+$ stromal cells.

CD49f is a cell surface protein that is widely distributed among cells of different tissues (CD49f. In: The Leukocyte Antigen Facts Book. Barclay A N, Brown M H, Law S K A, McKnight A J, Tomlinson M G van der Merwe P A (Eds.) Academic Press Inc., San Diego, USA, pp 267-8, 1997). In the epithelia, it is preferentially expressed by the cells in the basal compartment (Carter, W. G., Kaur, P., Gil, S. G., Gahr, P. J. & Wayner, E. A. J Cell Biol. 1990: 111, 3141-54). CD24 is widely distributed among cells of different tissues (CD24. In: The Leukocyte Antigen Facts Book. Barclay A N, Brown M H, Law S K A, McKnight A J, Tomlinson M G van der Merwe P A (Eds.) Academic Press Inc., San Diego, USA, pp 192-3, 1997). In the mammary gland, it is widely distributed through-out the epithelium and the stroma (FIG. 2). Many $CD45^+/Ter119^+/CD31^+/CD140a^+$ cells express either or both CD49f and CD24.

The present invention also relies on the observation that mammary cell populations enriched for stem cell activity ($CD45^-/Ter119^-/CD31^-/CD140a^-/CD49f^{++}/CD24^+$ phenotype) are deficient in CFCs since approximately 90% of all CFCs are luminal-restricted CFCs and have a slightly different phenotype in which CD49f is expressed at lower levels ($CD45^-/Ter119^-/CD31^-/CD140a^-/CD49f^+/CD24^+$).
Accordingly, the present invention allows one to distinguish the MaSC from the CFCs.

Figure 3:
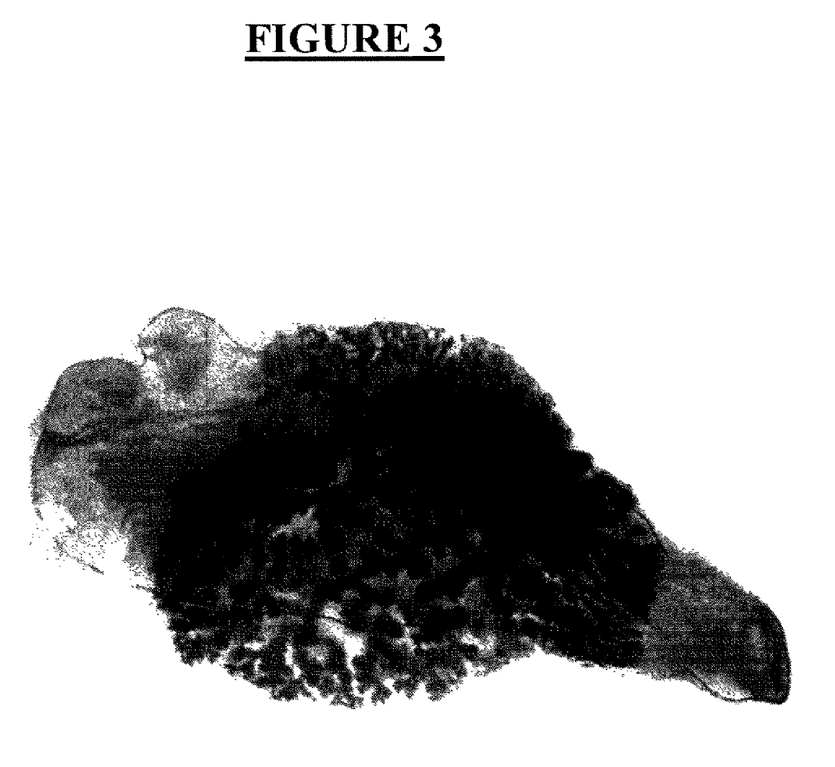
FIG. 3: Whole mount of a mouse mammary fat pad illustrating the outgrowth obtained by implanting a mouse MaSC.

The presence of stem cells can be detected by transplanting a cell suspension containing a stem cell into epithelium-free ("cleared") mouse mammary fat pads. Six weeks following implantation and pregnancy, engraftment can be detected by resecting the fat pad from the mouse and staining the fat pad with a dye to highlight the mammary tree. An example of an engrafted fat pad is illustrated in FIG. 3.

The inventors have determined that CD14 is strongly expressed among some of the luminal mammary epithelial cells and that approximately 89% of all Ma-CFCs in the luminal compartment express CD14. The inventors have also demonstrated that the CD14 gene transcript is upregulated in the Ma-CFC population. Luminal mammary epithelial cells are 80 times more abundant than stem cells. It is possible that the most common types of human breast cancer are initiated in luminal progenitor cells, since 70% of all human breast tumors have a luminal phenotype. Thus identification of cell surface markers on luminal mammary epithelial cells may be of great importance in breast cancer. CD14 is not expressed by any other cells of the mammary epithelium.

In addition, the inventors have found that the $CD14^+$ luminal progenitor population can be further subdivided into cells that are $Sca1^{high}$ and $Sca1^{low}$ as demonstrated in Example 5. Both the $CD14^+ Sca1^{high}$ and $CD14^+ Sca1^{low}$ subpopulations contain progenitor cells. A recent report has described the presence of two phenotypically distinct subpopulations within the luminal cell compartment of the mouse mammary gland (Sleeman K E and Smalley M J, unpublished): a steroid hormone (e.g. estrogen receptor) sensing population ($CD24^{high}Sca1^{high}$) and a milk protein expressing population ($CD24^{high}Sca1^{low}$). The inventors have examined the distribution of CD14, CD24 and Sca1 among luminal epithelial cells using multi-colour flow cytometric analysis, which revealed that three phenotypically distinct and separable subpopulations of cells may be identified, namely, $CD24^{high}CD14^+Sca1^{high}$, $CD24^{high}CD14^+ Sca1^{low}$, and $CD24^{high} CD14^-$. In vitro Ma-CFC analysis revealed that all progenitors reside within the $CD14^+$ subpopulation.

In another preferred embodiment, the method is used to enrich for mammary luminal restricted colony forming cells. Accordingly, the present invention provides a method of enriching for luminal restricted colony forming cells in a sample containing mammary cells comprising 1) reacting the sample with a first antibody composition capable of binding to antigens on non-epithelial cells under conditions so that conjugates are formed between the antibodies and the cells in the sample containing the non-epithelial antigens; 2) removing the conjugates; 3) recovering a cell preparation which is enriched in mammary epithelial cells; 4) reacting the sample enriched in epithelial cells with a second antibody composition capable of binding the antigens CD24 and/or CD14 under conditions so that conjugates form between antibodies and the cells in the sample containing the antigens CD24 and/or CD14; and 5) recovering the conjugates wherein the cells in the conjugates comprise luminal restricted colony forming cells.

Figure 4:
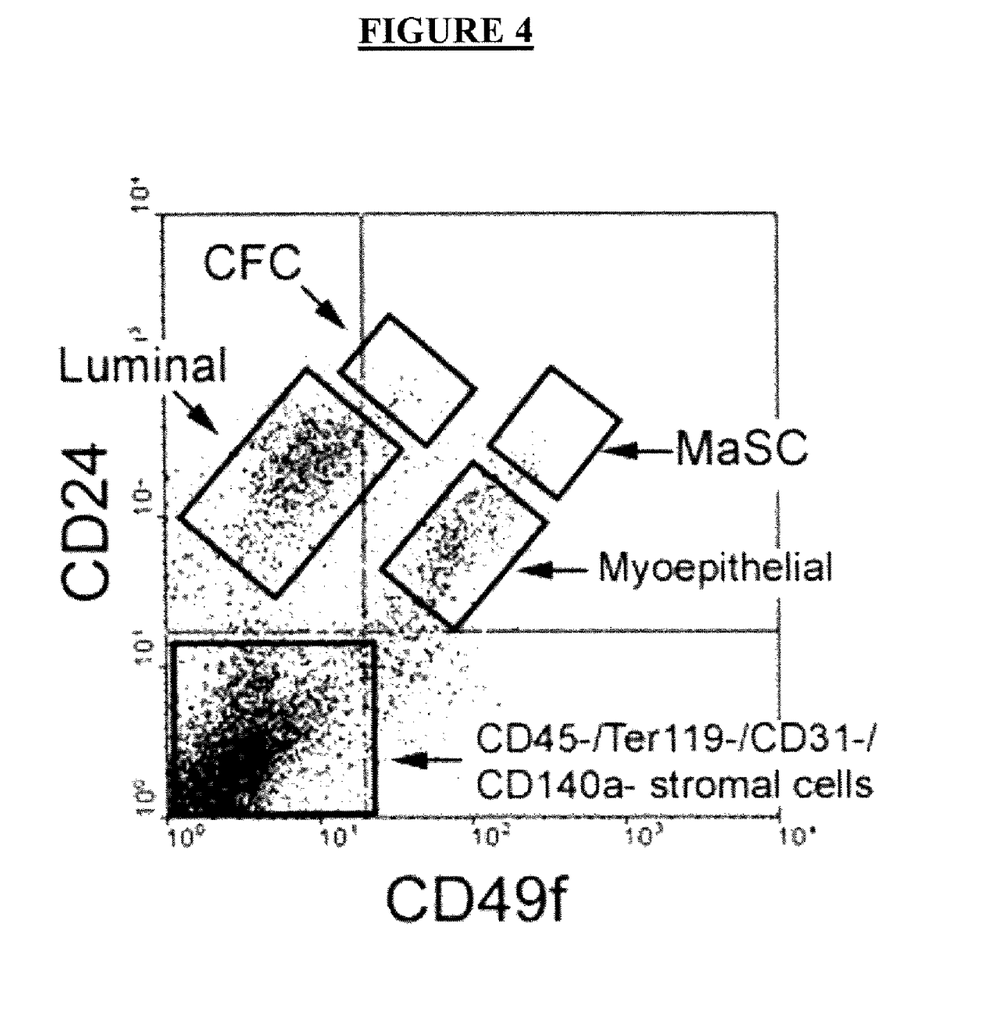
FIG. 4: FACS dot plot showing the distribution of $CD45^-/Ter119^-/CD31^-/CD140a^-$ cells according to their co-expression of CD24 and CD49f. The different cell subpopulations are indicated by circles and arrows.

When the present invention is used in a cell separation technology such as flow cytometry, the entire mammary epithelial hierarchy spanning from stem cells to differentiated luminal and myoepithelial cells can be visualized on a flow cytometry plot as illustrated in FIG. 4. Consequently, any of the mammary cell subpopulations can be identified and isolated to high purity. This method is superior to any method described to date since it no other method permits the differential isolation of MaSC and luminal-restricted CFCs. The method is also unique since there is no prior art describing the visualization of the mammary hierarchy.

Two general approaches may be used to differentially isolate the different subsets of mammary cells. The first is to label a portion of the non-epithelial component of the mammary cell suspension with antibodies specific for the cell surface epitopes CD45, Ter119, CD31 and CD140a and then to selectively deplete these cells by a negative selection strategy. Such strategies include directly or indirectly conjugating these antibodies to some type of a matrix such as magnetic beads, a panning surface, dense particles for density centrifugation, and adsorption column or an adsorption membrane. The leftover epithelial enriched population of mammary cells is then labeled with fluorochrome-conjugated antibodies specific for CD24 and CD49f, or CD24 and CD14 and the different epithelial cell subpopulations (as well as CD45$^-$/Ter119$^-$/CD31$^-$/CD140a$^-$ stromal cells) can be visualized by flow cytometry.

A second alternative method is to use stromal- and hematopoietic-specific (CD45/Ter119/CD31/CD140a) antibodies, CD24 antibodies, CD49f antibodies, and CD14 antibodies each conjugated directly or indirectly to a different fluorochrome. As a result, the contaminating CD45$^+$/Ter119$^+$/CD31$^+$/CD140a$^+$ stromal and hematopoietic cells can be gated out from the CD24, CD49f, and CD14 flow cytometry analysis.

The present invention relates to the method of differentially labeling mouse MaSC and luminal-restricted CFCs with antibodies specific for the CD24 and CD49f cell surface epitopes and the subsequent isolation of different subtypes of mammary cells, including MaSC and CFCs to high purities by flow cytometry.

The present invention also relates to the method of differentially labeling mouse Ma-CFCs with antibodies specific for the CD24 and CD14 cell surface epitopes and the subsequent isolation of different subtypes of Ma-CFCs, including luminal epithelial cells to high purities by flow cytometry.

The present invention relates to the antibody composition comprising antibodies specific for the CD24 and CD49f cell surface epitopes to differentially label mouse MaSC and luminal-restricted CFCs and to use this differential labeling strategy to isolate the different subtypes of mammary cells, including MaSC and CFCs to high purities by flow cytometry.

The present invention relates to the antibody composition comprising antibodies specific for the CD24 and CD14 cell surface epitopes to differentially label mouse Ma-CFCs and to use this differential labeling strategy to isolate the different subtypes of mammary cells, including epithelial luminal-restricted colony-forming cells to high purities by flow cytometry.

The antibodies used in the method of the invention may be labeled with a marker or they may be conjugated to a matrix. Examples of markers are biotin, which can be removed by avidin bound to a support, and fluorochromes, e.g. fluorescein, which provide for separation using fluorescence activated sorters. Examples of matrices are magnetic beads, which allow for direct magnetic separation (Kemshead J T. J Hematother 1992; 1:35-44), panning surfaces e.g. plates, (Lebkowski, J. S, et al., (1994), J. of Cellular Biochemistry supple. 18b:58), dense particles for density centrifugation (Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, Calif.), dense particles alone (Zwerner et al., Immunol. Meth. 1996 198(2): 199-202) adsorption columns (Berenson et al. 1986, Journal of Immunological Methods 91:11-19), and adsorption membranes.

The antibodies in the antibody compositions may be directly or indirectly coupled to a matrix. For example, the antibodies that bind non-epithelial cells in the compositions may be chemically bound to the surface of magnetic particles for example, using cyanogen bromide. When the magnetic particles are reacted with a sample, conjugates will form between the magnetic particles with bound antibodies specific for antigens on the surfaces of the non-epithelial cells and the cells having the antigens on their surfaces.

Alternatively, the antibodies may be indirectly conjugated to a matrix using antibodies. For example, a matrix may be coated with a second antibody having specificity for the antibodies in the antibody composition. By way of example, if the antibodies in the antibody composition are mouse IgG antibodies, the second antibody may be rabbit anti-mouse IgG.

The antibodies in the antibody compositions may also be incorporated in antibody reagents which indirectly conjugate to a matrix. Examples of antibody reagents are bispecific antibodies, tetrameric antibody complexes, and biotinylated antibodies.

Bispecific antibodies contain a variable region of an antibody in an antibody composition of the invention, and a variable region specific for at least one antigen on the surface of a matrix. The bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

A tetrameric immunological complex may be prepared by mixing a first monoclonal antibody which is capable of binding to at least one antigen on the surface of a matrix, and a second monoclonal antibody from the antibody composition of the invention. The first and second monoclonal antibody are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the F(ab')$_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

The antibodies of the invention may be biotinylated and indirectly conjugated to a matrix which is labeled with (strept) avidin. For example, biotinylated antibodies contained in the antibody composition of the invention may be used in combination with magnetic iron-dextran particles that are covalently labeled with (strept) avidin (Miltenyi, S. et al., Cytometry 11:231, 1990). Many alternative indirect ways to specifically cross-link the antibodies in the antibody composition and matrices would also be apparent to those skilled in the art.

In an embodiment of the invention, the cell conjugates are removed by magnetic separation using magnetic particles. Suitable magnetic particles include particles in ferrofluids and other colloidal magnetic solutions. "Ferrofluid" refers to a colloidal solution containing particles consisting of a magnetic core, such as magnetite (Fe$_3$O$_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. (1992) in J. Hematotherapy, 1:35-44, at pages 36 to 39, and Ziolo et al. Science (1994) 257:219 which are incorporated herein by reference. Colloidal particles of dextran-iron complex are preferably used in the process of the invention. (See Molday, R. S. and McKenzie, L. L. FEBS Lett. 170:232, 1984; Miltenyi et al., Cytometry 11:231, 1990; and Molday, R. S. and MacKenzie, D., J. Immunol. Methods 52:353, 1982; Thomas et al., J. Hematother. 2:297 (1993); and U.S. Pat. No. 4,452,733, which are each incorporated herein by reference).

In accordance with the magnetic separation method, the sample containing the epithelial cells to be recovered, is reacted with the above described antibody reagents, preferably tetrameric antibody complexes, so that the antibody reagents bind to the non-epithelial cells present in the sample to form cell conjugates of the targeted non-epithelial cells and the antibody reagents. The reaction conditions are selected to provide the desired level of binding of the targeted non-epithelial cells and the antibody reagents. Preferably the sample is incubated with the antibody reagents for a period of 5 to 60 minutes at either 4° or ambient room temperature. The concentration of the antibody reagents is selected depending on the estimated concentration of the targeted differentiated cells in the sample. Generally, the concentration is between about 0.1 to 50 µg/ml of sample. The magnetic particles are then added and the mixture is incubated for a period of about 5 minutes to 30 minutes at the selected temperature. The sample is then ready to be separated in a magnetic device.

The preparation containing non-magnetically labeled MaSC or CFC cells may be analyzed using procedures such as flow cytometry. The activity of the MaSC cells in the preparation may also be assessed for example by transplanting into mice as described previously.

III. Uses of the Compositions and Methods of the Invention

The invention may be used in the isolation of different subsets of mouse mammary cells including MaSC and luminal-restricted progenitor cells. These cells are of interest to breast cancer biologists, mammary gland biologists and developmental biologists. In particular, the ability to purify mammary progenitors and stem cells free of stromal cell contamination is important in determining the gene expression profiles of these cells and the factors that regulate their cell behaviour.

The invention includes kits for preparing samples enriched in mammary epithelial cells comprising antibodies that bind to non-epithelial cells in a mammary sample and instructions for the use thereof. The antibody composition for use in the kit preferably comprises antibodies that bind to CD45, Ter119, CD31 and CD140a.

The invention further includes kits for preparing samples enriched in MaSC or CFC cells comprising antibodies that bind to CD24 and/or CD49f and instructions for the use thereof.

The invention further includes a kit for preparing samples enriched in luminal restricted colony forming cells comprising a first set of antibodies that bind to non-epithelial cells and a second set of antibodies that bind to epithelial cells and instructions for the use thereof; wherein the first set of antibodies bind to CD45, Ter119, CD31 and optionally CD140a; and wherein the second set of antibodies bind to CD24 and/or CD14 for enriching luminal restricted colony forming cells.

The following non-limiting examples are illustrative of the present invention:

EXAMPLES

Example 1

Method for Separating Epithelial and Non-epithelial Cells in a Mammary Cell Sample Mammary glands from young adult female mice were removed and digested for 8 hours at 37° C. in EpiCult-B™ (StemCell Technologies, Vancouver, BC, Canada) supplemented with 5% fetal bovine serum (FBS) and 300 U/mL collagenase and 100 U/mL hyaluronidase (StemCell Technologies). At the end of this time, the preparation was vortexed and centrifuged at 450 g for 5 minutes. The supernatant was discarded and contaminating red blood cells lysed with an ammonium chloride wash. Following centrifugation, the cells were suspended in 2 mL of 0.25% trypsin prewarmed to 37° C. and further dissociated by gentle pipetting for 1-2 minutes. The cells were then washed once with 10 mL of Hank's Balanced Salt Solution supplemented with 2% FBS (HF) and incubated with 5 mg/mL dispase II (StemCell Technologies) and 0.1 mg/mL deoxyribonuclease I (StemCell Technologies) for 2 min at 37° C. The resultant cell suspension was diluted with HF and then filtered through a 40 µm mesh to obtain a single cell suspension.

Hematopoietic ($CD45^+$ and $Ter119^+$), endothelial ($CD31^+$) and stromal ($CD140a^+$) cells were removed by pre-incubating freshly dissociated cells in 2 µg/mL Fc receptor antibody 2.4G2 (American Type Culture Collection, Rockville, Md., USA) followed by a 10 minute incubation with biotin-conjugated antibodies specific for CD45 (clone 30-F11 from BD Pharmingen, San Diego, USA), Ter119 (clone Ter119 from BD Pharmingen), CD31 (clone MEC13.3 from BD Pharmingen) and with CD140a (clone APA5 from eBioscience, San Diego, Calif., USA). Antibody concentrations during the incubation process typically ranged from 0.5-2.0 µg/mL. Labeled cells (the non-epithelial cells) were then linked to magnetic nanoparticles using the EasySep™ Biotin Selection Kit (StemCell Technologies), and removed by placing the cell suspension in a magnet. Unlabeled cells ($CD45^-/Ter119^-/CD31^-/CD140a^-$) were poured off. These unlabeled cells are enriched for mammary epithelial cells.

Example 2

Method for Isolating Mammary Stem Cells or Luminal-restricted Colony Forming Cells from a Suspension of Mammary Epithelial Cells A suspension of mammary epithelial cells prepared as in Example 1 above, or prepared using flow cytometry, was labeled with antibodies recognizing epitopes of the cell surface proteins CD24 and CD49f. A suitable antibody clone specific for mouse CD24 is the M1/69 clone (BD Pharmingen). A suitable antibody clone specific for mouse CD49f is the GoH3 clone (BD Pharmingen). Both antibodies are used at a concentration of 1 µg/mL during the incubation process.

The CD24 and CD49f antibodies are directly conjugated to different fluorochromes that are also distinct from that used to identify the CD45+/Ter119+/CD31+/CD140a+ cells. Following treatment of the cell suspension with an agent to discriminate cells with non-intact plasma membranes (e.g., propidium iodide) the labeled cells were analyzed by flow cytometry and cells at any stage of differentiation from MaSC to differentiated luminal and myoepithelial cells were selectively isolated using fluorescence-activated cell sorting (FACS) (see FIG. 4).

Example 3

Assessment of the Colony Forming Cell and Mammary Stem Cell Content of Enriched Cell Populations The MaSC and CFC cell populations, isolated as described in Example 2, were then assessed for MaSC and CFC content by transplantation into cleared fat pads (Kordon E C, Smith G H. Development 1998; 12:1921-30) and by in vitro colony assays (Stingl J, Zandieh I, Eaves C J, Emerman J T. Breast Cancer Res Treat 2001:67:93-109), respectively. The MaSC fraction was found to be highly enriched from stem cells since approximately 80% of all stem cells present in the mouse mammary gland were in this subpopulation at a highly enriched frequency of 1 stem cell in 60 cells (from FVB mice) and 1 stem cell per 90 cells (from C57B1/6 mice). This represents an approximately 25-fold enrichment over non-sorted cells.

Self-renewal is the hallmark property of stem cells. To examine the self-renewal properties of MaSCs, 34 fat pads were transplanted with low numbers (11-42) of MaSC-enriched ($CD24^{med}CD49f^{high}$) cells. Because outgrowths were produced in only 11 of the 34 fat pads injected, most of these could be assumed to have arisen from a single MaSC. Secondary limiting dilution MaSC assays were performed on cell suspensions prepared from 4 of these 11 primary outgrowths, and the results demonstrated that they contained 25, 110, 190 and 1,200 MaSCs respectively. Thus, highly purified MaSCs could be shown to execute at least ten symmetrical self-renewal divisions.

The CFC fraction, identified in FIG. 4, was found to be highly purified for luminal-restricted CFCs, with approximately 1 CFC for every 6 sorted cells. This represented approximately 90% of all CFCs present in the mammary gland. The MaSC frequency in the CFC fraction is <1 in 230 sorted cells (FVB mice) and <1 in 6,100 sorted cells (C57B1/6 mice).

Example 4

Evaluation of the Gene Expression Profile of Mammary Stem and Progenitor Cells

The gene expression profile of MaSC- and CFC-enriched cell fractions isolated as described in Examples 1 and 2 was examined. Total ribonucleic acid (RNA) was isolated and the gene expression profiles of the different subsets of cells were analyzed by microarray analysis. The genes preferentially expressed by the different subsets of cells were identified. Affymetrix mouse MOE430 genome array chips indicated that the Ma-CFC-enriched cells contain higher levels of keratin 8, 18 and 19 transcripts and a variety of casein transcripts, also typical of luminal cells, in comparison to either the MaSC-enriched or myoepithelial cells. Conversely, transcripts for keratins 5 and 14, smooth muscle actin, smooth muscle myosin, vimentin and laminin, all of which show elevated expression in basal/myoepithelial cells, were found to be present at higher levels in the MaSC-enriched and myoepithelial populations. However, significant differences in gene expression were not evident when the latter two fractions were compared. The differences in keratin 14, 18 and 19 and smooth muscle actin transcript levels in the three populations studied were confirmed by quantitative real-time PCR analysis. Notably, transcripts for keratin 6, a putative progenitor cell marker, were also found to be highest in the fraction enriched in Ma-CFCs. This example is the first description of the gene expression profiles of highly purified mammary stem and progenitor cell fractions.

Example 5

Figure 5:
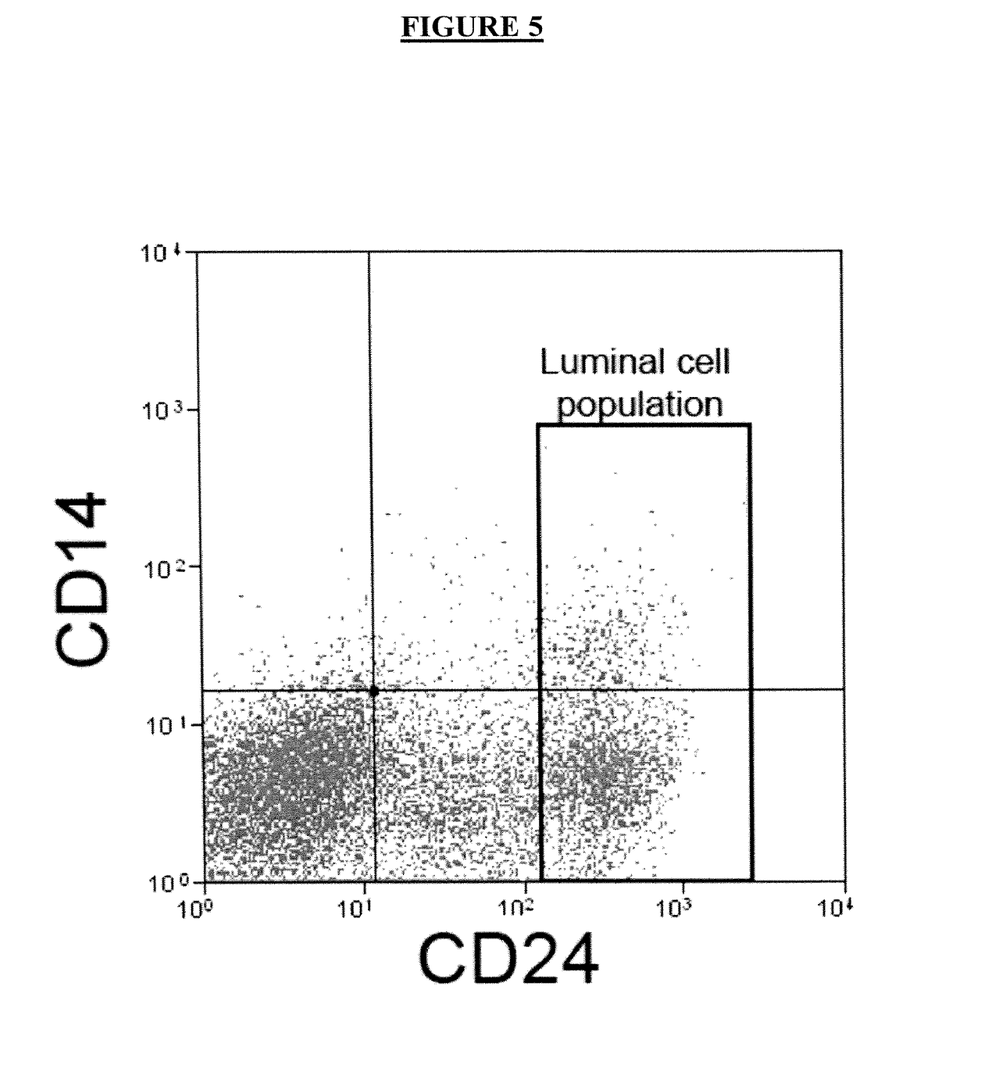
FIG. 5: FACS dot plot showing the distribution of $CD45^-/Ter119^-/CD31^-$ cells according to their co-expression of CD24 and CD14. The boxed area indicates the luminal cell population.
Figure 6:
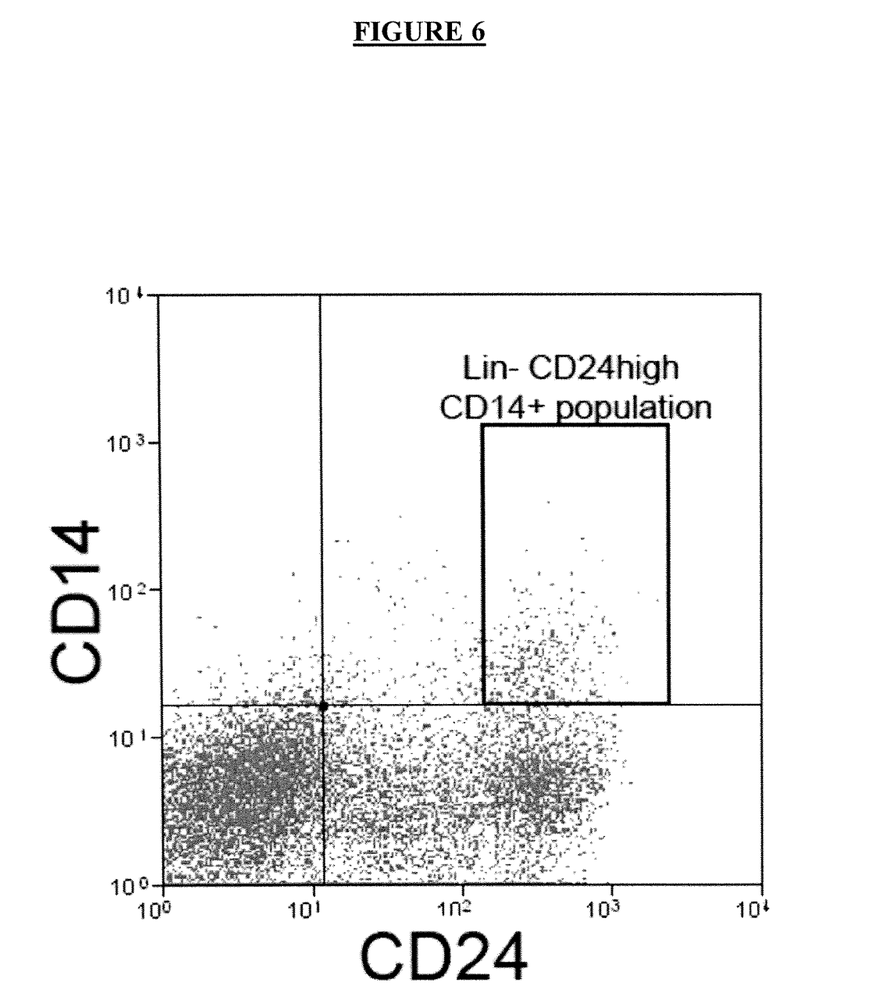
FIG. 6: FACS dot plot showing the distribution of $CD45^-/Ter119^-/CD31^-$ cells according to their co-expression of CD24 and CD14. The boxed area indicates the $Lin^- CD24^{high}CD14^+$ population.

Method for Isolating Mammary Luminal-Restricted Colony Forming Cells from a Suspension of Mammary Epithelial Cells A suspension of mammary epithelial cells was labeled with antibodies recognizing epitopes of the cell surface proteins CD45, CD31, Ter119, Sca1, CD24, and CD14. The anti-CD45, anti-CD31, and Ter119 antibodies were directly conjugated to the same fluorochromes and cells negative for all three of these markers together comprise the Lin⁻ fraction. The Sca1, anti-CD24, and anti-CD14 antibodies were each directly conjugated to different, distinct, fluorochromes. Following treatment of the cell suspension with an agent to discriminate cells with a non-intact cell membrane (e.g. propidium iodide), the labeled cells were analyzed by flow cytometry and various subpopulations of cells selectively isolated and evaluated in vitro colony assays (Stingl J, Zandieh I, Eaves C J, Emerman J T, Breast Cancer Res Treat 2001:67:93-109). The luminal cell population was found in the Lin⁻CD24$^{high}$ gate, as shown in FIG. 5. The Lin⁻CD24$^{high}$CD14+ fraction (see FIG. 6), which comprised only 19% of the luminal cells, nonetheless contained greater than 89% of all the luminal colony forming cells. The inventors have examined the distribution of CD14, CD24 and Sca1 among luminal epithelial cells using multi-colour flow cytometric analysis, which revealed that three phenotypically distinct and separable subpopulations of cells may be identified, namely, CD24$^{high}$CD14+Sca1$^{high}$, CD24$^{high}$CD14+Sca1$^{low}$, and CD24$^{high}$CD14⁻. Table II shows the proportion of luminal-restricted progenitors found in the various fractions.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE I

| Species | Luminal-restricted CFC Phenotype | Bipotent CFC phenotype | References |
|---|---|---|---|
| Human | EpCAM+/CD49f+/MUC1+/CD133+/CD10−/Thy-1− | EpCAM+/CD49f+/MUC1−/CD133−/CD10+/Thy-1+ | Stingl J, Eaves C J, Kuusk U, Emerman J T. Differentiation 1998; 63: 201-13. Stingl J, Zandieh I, Eaves C J, Emerman J T.. Breast Cancer Res Treat 2001: 67: 93-109. Stingl J, Raouf A, Emerman J T and Eaves C J. J Mammary Gland Biology Neoplasia 2005; 10: 49-59. O'Hare M J, Ormerod M G, Monaghan P, Lane E B, Gusterson B A. Differentiation 1991; 46: 209-21. Kao C Y, Nomata K, Oakley C S, Welsch C W and Chang C C. Carcinogenesis 1995; 16: 531-38. Kao C Y, Oakley C S, Welsch C W, Chang C C. In Vitro Cell Dev Biol Anim 1997; 33: 282-88. Stingl J, Eaves C J, Emerman J T. In: Ip M and Asch B B, editors. Methods in Mammary Gland Biology and Breast Cancer Research. New York (NY): Kluwer Academic/Plenum Publishers; 2000. p. 177-93. Clarke C, Titley J, Davies S and O'Hare M J. Epithelial Cell Biol 1994; 3: 38-46. |
| Rat | Peanut Agglutinin binding+ Thy-1− | | Kim N D and Clifton K H. Experimental Cell Res 1993; 207: 74-85. |
| | MUC1+ | CD10+ | Dundas S R, Ormerod M G, Gusterson B A, O'Hare M J. J Cell Sci 1991; 100: 459-71. |
| Mouse | CD45−/CD49f−/Sca-1$^{low}$/PNA+ | | Stingl J, Ricketson I, Choi D, Eaves C J. Proceed Am Assoc Cancer Res 2004; 45: 641-2. |
| | mMFGM+ | JB6 epitope+ | Smalley M J, Titley J and O'Hare M J. In Vitro Cell Dev Biol-Animal 1998; 34; 711-721. | mMFGM = mouse milk fat globule membrane
JB6 = antibody of unknown epitope specificity

TABLE II

Proportion of luminal-restricted progenitors found in the various subpopulations

| Subpopulation | Proportion of all progenitors (%) Mean ± sem (n = 5) |
|---|---|
| Total luminal | 100 |
| CD14+ Sca1$^{high}$ | 39 ± 11 |
| CD14+ Sca1$^{low}$ | 46 ± 8 |
| CD14− | 9 ± 2 |

All subpopulations shown are also Lin−CD24$^{high}$.

REFERENCES

Al-Hajj M, Wicha M S, Benito-Hernandez A, Morrison S J, Clarke M F. Proc Natl Acad Sci USA. 2003; 100:3983-8.

Berenson et al. 1986, Journal of Immunological Methods 91:11-19.

CD24. In: The Leukocyte Antigen Facts Book. Barclay A N, Brown M H, Law S K A, McKnight A J, Tomlinson M G van der Merwe P A (Eds.) Academic Press Inc., San Diego, USA, pp 192-3, 1997.

CD31. In: The Leukocyte Antigen Facts Book. Barclay A N, Brown M H, Law S K A, McKnight A J, Tomlinson M G van der Merwe P A (Eds.) Academic Press Inc., San Diego, USA, pp 206-8, 1997.

CD45. In: The Leukocyte Antigen Facts Book. Barclay A N, Brown M H, Law S K A, McKnight A J, Tomlinson M G van der Merwe P A (Eds.) Academic Press Inc., San Diego, USA, pp 244-47, 1997.

CD49f. In: The Leukocyte Antigen Facts Book. Barclay A N, Brown M H, Law S K A, McKnight A J, Tomlinson M G van der Merwe P A (Eds.) Academic Press Inc., San Diego, USA, pp 267-8, 1997.

Carter, W. G., Kaur, P., Gil, S. G., Gahr, P. J. & Wayner, E. A. J Cell Biol. 1990: 111, 3141-54.

Clarke C, Titley J, Davies S and O'Hare M J. Epithelial Cell Biol 1994; 3: 38-46.

Crowley M. R., Bowtell D. and Serra R. Dev Biol 279:58-72.

Dundas S R, Ormerod M G, Gusterson B A, O'Hare M J. J Cell Sci 1991; 100:459-71.

Kao C Y, Nomata K, Oakley C S, Welsch C W and Chang C C. Carcinogenesis 1995; 16:531-38.

Kao C Y, Oakley C S, Welsch C W, Chang C C. In Vitro Cell Dev Biol Anim 1997; 33:282-88.

Kemshead J T. J Hematother 1992; 1:35-44.

Kim N D and Clifton K H. Experimental Cell Res 1993; 207: 74-85.

Kina T, Ikuta K, Takayama E, Wada K, Majumdar A S, Weissman I L, Katsura Y. Br J. Haematol. 2000; 109: 280-7.

Kordon E C, Smith G H. Development 1998; 125:1921-30.

Lebkowski, J. S, et al., (1994), J. of Cellular Biochemistry supple. 18b:58

Miltenyi, S. et al., Cytometry 11:231, 1990

Molday, R. S. and MacKenzie, D., J. Immunol. Methods 52:353, 1982
Molday, R. S. and McKenzie, L. L. FEBS Lett. 170:232, 1984;
O'Hare M J, Ormerod M G, Monaghan P, Lane E B, Gusterson B A. Differentiation 1991; 46:209-21.
Orr-Urtreger A, Lonai P. Development. 1992; 115:1045-58.
Perez et al., (1985 Nature 316:354
Smalley M J, Titley J and O'Hare M J. In Vitro Cell Dev Biol-Animal 1998; 34; 711-721.
Staerz et al., (1985, Nature, 314:628)
Staerz & Bevan, (1986, PNAS (USA) 83: 1453
Staerz & Bevan, (1986, Immunology Today, 7:241
Stingl J, Eaves C J, Kuusk U, Emerman J T. Differentiation 1998; 63:201-13.
Stingl J, Eaves C J, Emerman J T. In: Ip M and Asch B B, editors. Methods in Mammary Gland Biology and Breast Cancer Research. New York (NY): Kluwer Academic/Plenum Publishers; 2000. p. 177-93.
Stingl J, Zandieh I, Eaves C J, Emerman J T. Breast Cancer Res Treat 2001:67:93-109.
Stingl J, Ricketson I, Choi D, Eaves C J. Proceed Am Assoc Cancer Res 2004; 45:641-2.
Stingl J, Raouf A, Emerman J T and Eaves C J. J Mammary Gland Biology Neoplasia 2005; 10:49-59.
Thomas et al., J. Hematother. 2:297 (1993)
Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, Calif.
Welm B E, Tepera S B, Venezia T, Graubert T A, Rosen J M, Goodell M A. Dev Biol 2002; 245:42-56.
Ziolo et al. Science (1994) 257:219
Zwerner et al., Immunol. Meth. 1996 198(2):199-202

We claim:

1. A method of enriching luminal restricted colony forming cells in a sample containing mammary cells comprising 1) reacting the sample with a first antibody composition comprising antibodies that bind to the antigens CD45, Ter119 and CD31 on non-epithelial cells under conditions so that conjugates are formed between the antibodies and the cells in the sample containing the non-epithelial antigens; 2) removing the conjugates; 3) recovering a cell preparation which is enriched in mammary epithelial cells; 4) reacting the sample enriched in epithelial cells with a second antibody composition capable of binding the antigens CD24 and/or CD14 under conditions so that conjugates form between antibodies and the cells in the sample containing the antigens CD24 and/or CD14; and 5) recovering the conjugates wherein the cells in the conjugates comprise luminal restricted colony forming cells.

2. The method according to claim 1 wherein the mammary cells are mouse cells.

3. The method according to claim 1 wherein the mammary cells are normal cells.

4. The method according to claim 1 wherein the epithelial cells consist of differentiated cells, CFCs or stem cells.

5. The method according to claim 1 wherein the first antibody composition further comprises antibodies that bind to CD140a.

6. The method according to claim 1 wherein the second antibody composition comprises antibodies that bind to CD24.

7. The method according to claim 1 wherein the second antibody composition comprises antibodies that bind to CD14.

8. The method according to claim 1 wherein the second antibody composition comprises antibodies that bind to CD24 and CD14.

9. The method according to claim 1 wherein the antibodies in the antibody compositions are monoclonal antibodies.

10. The method according to claim 9 wherein the antibodies in the antibody composition are labeled with a marker or the antibodies are conjugated to a matrix.

11. The method according to claim 9 wherein the antibodies in the antibody composition are labeled with biotin or a fluorochrome.

12. The method according to claim 10 wherein the matrix is magnetic beads, a panning surface, dense particles for density centrifugation, an adsorption column, or an adsorption membrane.

13. The method according to claim 10 wherein each of the monoclonal antibodies in the first antibody composition is incorporated in a tetrameric antibody complex which comprises a first monoclonal antibody of a first animal species from the first antibody composition and a second monoclonal antibody of the first animal species which is capable of binding to at least one antigen on the surface of a matrix, which have been conjugated to form a cycle tetramer with two monoclonal antibodies of a second animal species directed against the Fc-fragments of the antibodies of the first animal species.

14. The method according to claim 1 wherein a fluorescence-activated cell sorter can be used to identify and purify cell-antibody conjugates in the second antibody composition.

15. The method according to claim 1 wherein the mouse mammary cells are obtained from freshly dissociated mouse mammary glands.

* * * * *